United States Patent [19]

Hashimoto et al.

[11] Patent Number: 4,702,816
[45] Date of Patent: Oct. 27, 1987

[54] OXYGEN CONCENTRATION DETECTION SYSTEM

[75] Inventors: Kenshiro Hashimoto; Yasushi Okada, both of Wako, Japan

[73] Assignee: Honda Giken Kogyo Kabushiki Kaisha, Tokyo, Japan

[21] Appl. No.: 841,512

[22] Filed: Mar. 19, 1986

[30] Foreign Application Priority Data

Mar. 19, 1985 [JP] Japan ................................ 60-56344
Sep. 7, 1985 [JP] Japan ................................ 60-199211

[51] Int. Cl.$^4$ ............................................. G01N 27/30
[52] U.S. Cl. ................................... 204/406; 204/421; 204/425; 204/15
[58] Field of Search ............... 204/15, 412, 421, 425, 204/427, 431, 406

[56] References Cited

U.S. PATENT DOCUMENTS 4,440,621 4/1984 Kitahara ............................. 204/406
4,586,476 5/1986 Asayama ............................ 123/440
4,609,452 9/1986 Shimomura ........................ 204/425

Primary Examiner—John F. Niebling
Assistant Examiner—Ben Hsing
Attorney, Agent, or Firm—Birch, Stewart, Kolasch & Birch

[57] ABSTRACT

An oxygen concentration detection system includes an oxygen sensor unit sensitive to oxygen in ambient oxygen-containing gases, an activating current supply operative to supply an activating current to the oxygen sensor unit. The oxygen sensor unit is responsive to the activating current and operative to produce a sensor signal voltage variable with the concentration of oxygen in the oxygen-containing gases. A reference signal generator produces a predetermined reference signal, the activating current supply means is responsive to the reference signal for producing the activating current. A current limiting circuit limits the oxygen concentration below a predetermined value which is variable with one of the activating current and the sensor signal voltage.

8 Claims, 6 Drawing Figures

OXYGEN CONCENTRATION DETECTION SYSTEM

FIELD OF THE INVENTION

The present invention relates to an oxygen concentration detection system for determining the concentration of oxygen in an oxygen-containing atmosphere in an enclosed volume and, more particularly, to an oxygen concentration detection system using an electrochemical oxygen sensor unit adapted to determine the concentration of oxygen in, typically, exhaust gases from an automotive internal combustion engine.

BACKGROUND OF THE INVENTION

Various feedback mixture control systems are known and used to clean exhaust gases from automotive internal combustion engines. Such a mixture control system typically uses an electric signal generated by an oxygen sensor adapted to detect and determine the concentration of oxygen in the exhaust gases from the engine. The electric signal produced by the oxygen sensor is processed in accordance with such schemes as to clean the exhaust gases from the engine and enables the control system to properly regulate the air-to-fuel ratio of the combustible mixture to be inducted into the power cylinders of the engine.

Among the various types of oxygen sensors used for such exhaust-gas cleaning purposes, there is an electrochemical oxygen sensor device using an oxygen-ion conductive solid electrolyte as an active material. Examples of a sensor device of this type are disclosed in U.S. Pat. No. 4,450,065 and Japanese Provisional Patent Publication No. 58-153155. The electrochemical oxygen sensor device shown in each of these is operative to generate a current or voltage output which varies in proportion to the detected concentration of oxygen.

Such an oxygen sensor unit largely consists of a combination of oxygen pump and sensor cell stacks or elements each comprising a pair of spaced electrode plates and an active layer of an oxygen-ion conductive solid electrolyte sandwiched between the electrode plates. The pump and cell stacks are spaced apart in parallel from each other to form between the respective inner electrode plates of the stacks a gap which is exposed to a passageway in, for example, the exhaust manifold of an internal combustion engine when the sensor device is in use. Typically, the electrode plates of the oxygen pump stack are subjected to a current so that the inner electrode plate is negative in polarity with respect to the outer electrode plate.

When a d.c. current is applied to the oxygen pump stack of the sensor device thus largely constructed, oxygen ions are caused to migrate through the oxygen-ion conductive active layer of the oxygen pump stack away from the negative inner electrode plate toward the positive outer electrode plate of the stack. As a result of such movement of oxygen ions through the active layer of the oxygen pump stack, the oxygen molecules contained in the exhaust gases in the gap between the pump and cell stacks are caused to diffuse into the active layer through the inner electrode plate, causing the same number of oxygen molecules to leave the active layer through the outer electrode plate of the oxygen pump stack. As the oxygen molecules are pumped out of the gap between the pump and cell stacks into the active layer of the oxygen pump stack, there accordingly is produced a gradual decrease in the concentration of oxygen in the gap so that a differential grows between the concentrations of oxygen in the gases in the gap and in the ambient gases in which the sensor unit is immersed within the exhaust manifold of the engine. Under a steady state condition which is then reached, a differential oxygen partial pressure is thus developed between the fluxes of the gases inside and outside the gap and acts on the oxygen-ion conductive active layer of the sensor cell stack. The sensor cell stack is accordingly caused to induce across the active layer thereof an electromotive force which varies with the differential between the pumped and non-pumped oxygen partial pressures. Such an electromotive force and accordingly the voltage (cell voltage) across the sensor cell stack varies with the concentration of the oxygen in the ambient exhaust gases if the current (pump current) applied to the oxygen pump stack is controlled to remain constant in order to maintain the concentration of the oxygen in the gap constant. If the cell voltage is maintained constant, the pump current varies widely. The pump current controlled to vary in this fashion is substantially proportional to the concentration of the oxygen in the ambient exhaust gases to which the oxygen sensor is subjected and can thus be used as a signal current in the aforesaid feedback mixture control system for an internal combustion engine.

If it happens that an excess of pump current is fed to the oxygen pump stack of the oxygen sensor unit, more oxygen molecules are pumped out of the oxygen-ion conductive active layer of the oxygen pump stack than those injected into the layer, which is accordingly deprived of an excess of oxygen molecules to create an oxygen-depleted state therein. This phenomenon is known as the "blackening" of the oxygen-ion conductive solid electrolyte used as the active material in the oxygen sensor unit. Where a solid electrolyte of, for example, zirconia (zirconium oxide, $ZrO_2$) is used as the solid electrolytic substance, the zirconium component is separated from the active layer as a result of the blackening of the electrolytic substance. The blackening of the active layer of the oxygen pump stack causes accelerated deterioration of the pump stack and prevents the oxygen sensor unit from properly functioning.

With a view to precluding an occurrence of such blacking of the oxygen-ion conductive active layer of the oxygen pump stack, a feedback mixture control system using an oxygen sensor unit of the described nature is usually designed to limit the pump current below a critical value which varies with the concentration of oxygen detected by the sensor unit. The pump or activating current to be supplied to the oxygen pump stack is thus controlled to stay below such a critical value and is compared with a certain reference current to determine whether the air-to-fuel ratio of the mixture to be supplied to the power cylinders of the engine is to be shifted to the rich burn side or to the lean burn side. Such control of the air-to-fuel ratio of the mixture is usually effected by introducing secondary air through a secondary air introducing control valve. The secondary air introducing control valve is operated to shift the air-to-fuel ratio of the mixture to the lean burn side when made open and to shift the air-to-fuel ratio to the rich burn side when closed. The valve is operated to open and close depending upon the control signal produced on the basis of the pump current varied as above discussed. By the alternate opening and closing actions of such a secondary-air introducing control valve, the air-to-fuel ratio of the mixture to be supplied to the power cylinders of the engine is controlled toward a value represented by the reference current with which the pump current was compared.

FIG. 1 of the drawings is representative of the critical value of the pump current ($I_p$) over which the oxygen-ion conductive active layer of the oxygen pump stack might cause the blackening when the oxygen sensor unit is placed in an atmosphere containing oxygen in a given concentration. As will be seen from this characteristic curve, the critical value of shown by the line d of FIG. 1 becomes the smaller and the pump current $I_p$ as the detected concentration of oxygen becomes smaller with the mixture supplied to the power cylinders of the engine made richer. When the mixture to be supplied to the power cylinders of the engine happens to be suddenly enriched for one reason or another (with, for example, the throttle valve in the induction system of the engine closed suddenly to deceleration), the secondary-air introducing control valve is actuated to open to supply additional air into the mixture immediately upon enrichment of the mixture. The pump current $I_p$ supplied to the oxygen sensor unit after the mixture has thus been leaned out subsequently to the sudden enrichment however increases beyond the critical value for the concentration of oxygen to result from the leaned mixture and would cause the blackening of the active layer of the oxygen pump stack. The pump current $I_p$ unchanged and is indicative of the oxygen concentration resulting from the enriched mixture for some time after the mixture is leaned out subsequently to the sudden enrichment. This is because of the fact that there inevitably exists a certain amount of time lag before the result of the combustion of the mixture diluted with the additional air is responded to by the oxygen sensor unit in the exhaust manifold after the mixture was leaned out in the induction system of the engine.

It is accordingly a prime object of the present invention to provide an improved oxygen concentration detection system having an electrochemical oxygen sensor unit which is provided with means to reliably protect the oxygen pump stack of the sensor unit from causing the blackening phenomenon which would otherwise be caused by an excess of pump current applied to the oxygen pump stack.

It is another important object of the present invention to provide an improved oxygen concentration detection system in which, when used in the exhaust system of an internal combustion engine, the oxygen sensor unit forming part of the system can be reliably protected from causing the blackening of the oxygen pump stack provided therein.

SUMMARY OF THE INVENTION

In accordance with one important aspect of the present invention, there is provided an oxygen concentration detection system comprising (1) an oxygen sensor unit sensitive to oxygen in ambient oxygen-containing gases, (2) activating current supply means operative to supply an activating current to the oxygen sensor unit, (3) the oxygen sensor unit being responsive to the activating current and operative to produce a sensor signal voltage variable with the concentration of oxygen in the oxygen-containing gases, (4) reference signal generator means operative to produce a predetermined reference signal, (5) the activating current supply means being responsive to the reference signal for producing the activating current, and (6) current limiting means for limiting the oxygen concentration below a predetermined value which is variable with one of the activating current and the sensor signal voltage.

In accordance with another important aspect of the present invention, there is provided an oxygen concentration detection system comprising (1) an oxygen sensor unit sensitive to oxygen in ambient oxygen-containing gases, (2) activating current supply means operative to supply an activating current to the oxygen sensor unit, (3) the oxygen sensor unit being responsive to the activating current and operative to produce a sensor signal voltage variable with the concentration of oxygen in the oxygen-containing gases, (4) reference voltage generator means operative to produce a predetermined reference voltage at which the sensor signal voltage is to be maintained constant, (5) the activating current supply means being responsive to the reference voltage and further operative to control the activating current to vary in a manner to maintain the sensor signal voltage substantially equal to the reference voltage so that the activating current is variable with the concentration of oxygen in the ambient oxygen-containing gases, (6) means for producing a first predetermined current value, (7) current limiting means for comparing the activating current with the first predetermined current value and allowing the reference voltage generator means to maintain the reference voltage if the activating current is less than the first predetermined current value or causing the activating current supply means to cease the supply of the activating current to the oxygen sensor unit if the activating current is not less than the first predetermined current value.

In accordance with still another important aspect of the present invention, there is provided an oxygen concentration detection system comprising (1) an oxygen sensor unit sensitive to oxygen in ambient oxygen-containing gases, (2) activating current supply means operative to supply an activating current to the oxygen sensor unit, (3) the oxygen sensor unit being responsive to the activating current and operative to produce a sensor signal voltage variable with the concentration of oxygen in the oxygen-containing gases, (4) reference voltage generator means operative to produce a predetermined reference voltage at which the activating current is to be maintained constant, (5) sensor signal voltage generating means for producing a sensor signal voltage variable with the activating current, (6) the activating current supply means being responsive to the reference voltage and further operative to control the activating current to vary in a manner to maintain the activating current constant so that the sensor signal voltage is variable with the concentration of oxygen in the ambient oxygen-containing gases, (7) means for producing a first predetermined voltage value, and (8) current limiting means for comparing the sensor signal voltage with a first predetermined voltage value and allowing the reference voltage generating means to maintain the activating current if the sensor signal voltage is less than the first predetermined voltage value or causing the activating current supply means to terminate the supply of the activating current to the oxygen sensor if the sensor signal voltage is greater than the first predetermined voltage value, (9) the activating current supply means being further responsive to the differential voltage and, in the presence of the differential voltage, being further operative to control the activating current so that the sum of the sensor signal voltage and the differential voltage is substantially equal to the reference voltage.

BRIEF DESCRIPTION OF THE DRAWINGS

The features and advantages of an oxygen concentration detection system according to the present invention will be more clearly appreciated from the following description taken in conjunction with the accompanying drawings in which.

DESCRIPTION OF THE PREFERRED EMBODIMENTS

FIRST EMBODIMENT

Construction and Arrangement

Figure 2:
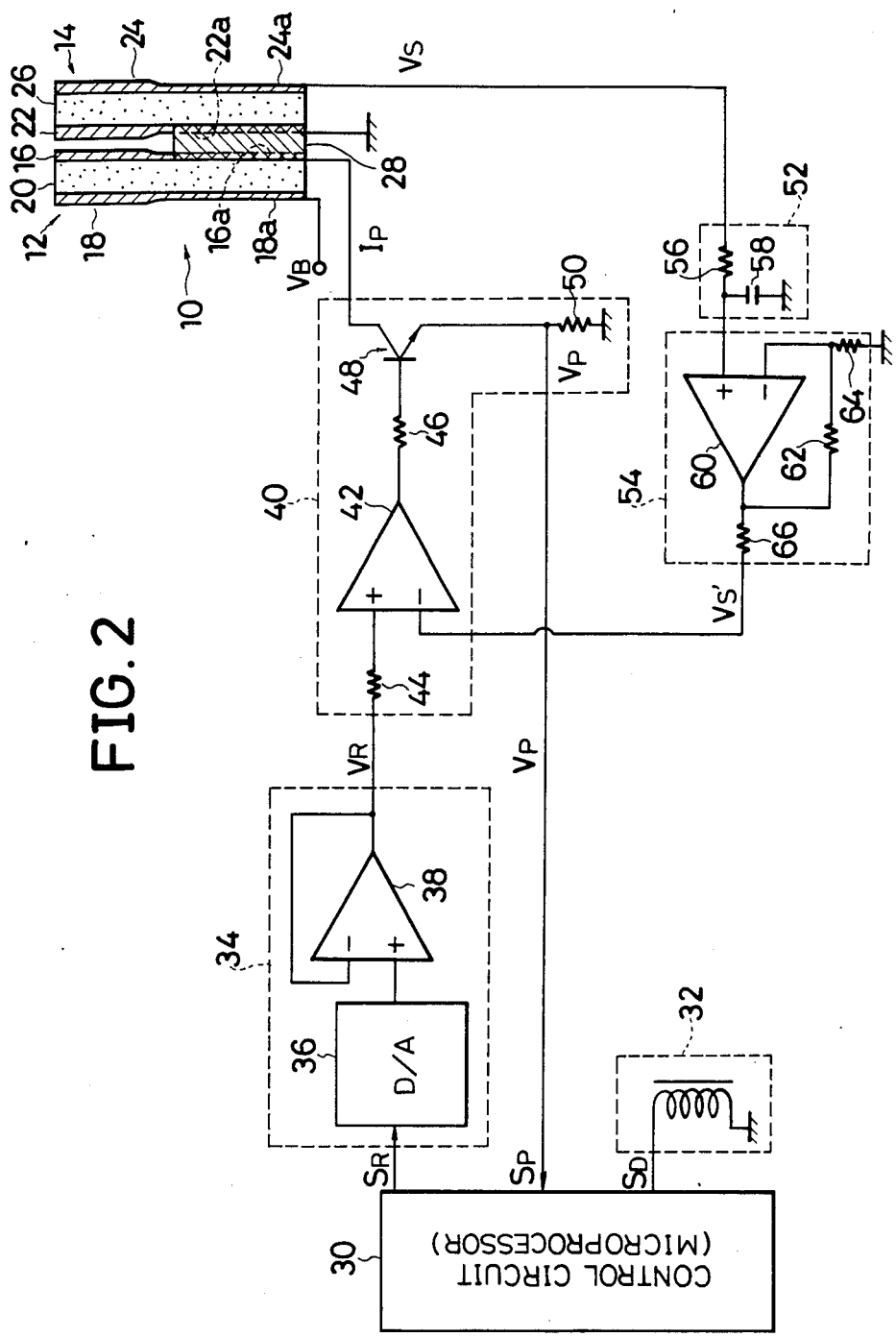
FIG. 2 is a block diagram showing the general circuit arrangement of a first preferred embodiment of a oxygen concentration detection system according to the present invention with the oxygen sensor unit of the system shown in section.

Referring to FIG. 2 of the drawings, an oxygen concentration detection system embodying the present invention comprises an electrochemical oxygen sensor unit 10. The oxygen sensor unit 10 of the embodiment herein shown is provided in the form of a multi-layer structure which largely consists of an oxygen pump stack 12 and a sensor cell stack 14. The oxygen pump stack 12 comprises a pair of inner and outer electrode plates 16 and 18 which are spaced apart in parallel from each other and an active layer 20 which is closely sandwiched between the electrode plates 16 and 18. Likewise, the sensor cell stack 14 comprises a pair of inner and outer electrode plates 22 and 24 spaced apart in parallel from each other and an active layer 26 closely sandwiched between the electrode plates 22 and 24. The pump and cell stacks 12 and 14 are spaced apart in parallel from each other to form a gap between the respective inner electrode plates 16 and 22 of the stacks 12 and 14 and are coupled together by a spacer layer 28 sandwiched between the respective active layers 20 and 26 of the pump and cell stacks 12 and 14. Each of the active layers 20 and 26 is constructed of an oxygen-ion conductive solid electrolyte. Examples of such an electrolytic substance include a solid solution of zirconia (zirconium oxide, $ZrO_2$) mixed with yttria (yttrium oxide, $Y_2O_3$) or calcia (calcium oxide, $CaO$) as a solute although another type of solid solution such as, for example, cerium dioxide ($CeO_2$), thorium dioxide ($ThO_2$) or hafnium dioxide ($HfO_2$) could also be used. Each of the electrode plates 16, 18, 22 and 24 is formed preferably of platinum, rythenium or palladium and may be formed by frame spraying, chemical plating or vacuum deposition techniques using any of these substances. The spacer layer 28 formed between the pump and cell stacks 12 and 14 may be of any heat-resistive, electrically non-conductive, inorganic adhesive such as a ceramic adhesive. The electrode plates 16 and 18 of the oxygen pump stack 12 merge into elongated strip portions 16a and 18a and, likewise, the electrode plates 22 and 24 of the sensor cell stack 14 merge into elongated strip portions 22a and 24a. The strip portions thus formed on the active layer of each of the pump and cell stacks 12 and 14 provide leads for the stack.

Figure 1:
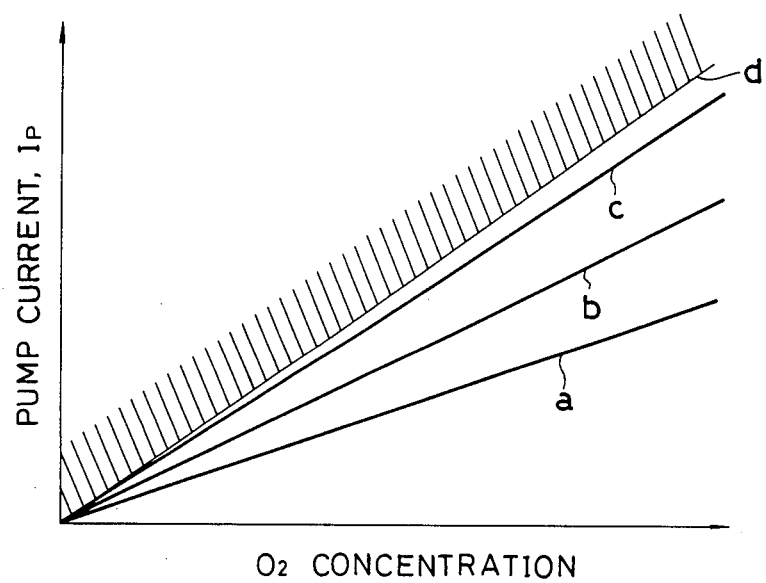
FIG. 1 is a graphic representation of a few examples of the relationship between the concentration of oxygen to which an oxygen sensor unit is subjected and the pump current ($I_P$) supplied to the sensor unit in response to the oxygen concentration with different constant cell voltages ($V_S$) produced across the sensor cell stack of the oxygen sensor unit, and of the range of the pump current $I_P$ over which the oxygen-ion conductive active layer of the pump stack might cause the blackening.

Though not shown in FIG. 1, the oxygen sensor unit 10 may further comprise insulator layers bonded or otherwise securely attached to the outer faces of the outer electrode plates 18 and 24 of the pump and cell stacks 12 and 14, respectively. Each of these insulator layers is formed of an electrically insulating inorganic substance and is provided with an opening allowing the underlying electrode plate to be partly open therethrough. The openings thus formed in the two insulator layers are located in registry with each other across the four electrode plates and two active layers of the sensor unit 10. Each insulator layer has embedded therein or received thereon a heat generating element which is provided typically in the form of an electrically and thermally resistive wire of metal such as for example platinum or gold. The insulators thus provided with such heat generating elements form part of temperature adjust means to maintain the temperature of the active layer of each of the pump and cell stacks 12 and 14 constant throughout operation of the oxygen sensor unit 10 placed in, for example, the exhaust manifold of an internal combustion engine.

The oxygen sensor unit 10 herein shown is assumed to be mounted on the exhaust system of an internal combustion engine (not shown). The oxygen sensor unit 10 is thus at least in part located within a passageway in the exhaust manifold and forms part of a feedback mixture control system to control the air-to-fuel ratio of the combustible mixture to be supplied to the power cylinders of the engine for the purpose of cleaning exhaust gases from the engine.

The oxygen sensor unit 10 thus constructed is electrically connected across a circuitry including a control circuit 30. The control circuit 30 is provided typically in the form of a microprocessor and has a reference signal output terminal $S_R$, a pump signal input terminal $S_P$, and a valve drive terminal $S_D$. From the reference signal output terminal $S_R$ of the control circuit 30 is supplied a digital signal which is normally representative of a fixed value at which the cell voltage ($V_S$) produced by the sensor cell stack 14 of the oxygen sensor unit 10 is to be maintained to provide a target air-to-fuel ratio in the mixture to be produced in the engine, as will be described. The output terminal $S_R$ may thus be implemented by a plurality of ports for supplying binary signals in a parallel form. At the pump signal input terminal $S_P$ of the control circuit 30 is to appear the pump voltage ($V_P$) produced in the system as will be seen as the description proceeds. The pump voltage $V_P$ supplied to this input terminal $S_P$ is memorized in the RAM (not shown) incorporated in the microprocessor constituting the control circuit 30. The digital signal to be supplied from the reference signal output terminal $S_R$ is given in the form of, for example, a four-bit digital signal and represents a value selected or calculated by the control circuit 30 on the basis of certain parameters including the pump voltage $V_P$ supplied to the pump signal input terminal $S_P$.

On the other hand, the valve drive terminal $S_D$ of the control circuit 30 is connected through a suitable interface circuit (not shown) to a solenoid-operated secondary-air introducing control valve 32 which forms part of the secondary air feed means for the engine in which the oxygen sensor unit 10 is provided. As well known in the art, such secondary air feed means includes a secondary-air circulation passageway leading to the induction system of the engine across the valve 32. The secondary-air circulation passageway is open into the induction system of the engine typically downstream of the throttle valve of the induction system, though not shown in the drawings and the valve 32 is made open to shift the air-to-fuel ratio of the mixture to the lean burn side and is closed to shift the air-to-fuel ratio to the rich burn side depending upon the control signal produced on the basis of the pump voltage $V_P$ supplied to the input terminal $S_P$ of the control circuit 30. By the opening and closing actions of such a secondary-air circulation control valve 32, the air-to-fuel ratio of the mixture to be supplied to the power cylinders of the engine is controlled to vary toward a value which corresponds to the concentration of oxygen represented by the digital signal supplied from the reference signal output terminal $S_R$ of the control circuit 30.

The digital signal from the reference signal output terminal $S_R$ of the control circuit 30 is thus fed to a programmable reference voltage generator network 34 which largely consists of a digital-to-analog converter (D/A) 36 and a voltage follower circuit 38. The digital-to-analog converter 36 receives the digital signal from the output terminal $S_R$ of the control circuit 30 and produces an analog output signal which is variable with the digital signal received from the control circuit 30. The voltage follower circuit 38 is formed of a unity-gain operational amplifier which acts as a buffer amplifier to eliminate the interaction between the digital-to-analog converter 36 and the network subsequent to the reference voltage generator network 34. The reference voltage generator network 34 is thus operative to produce at the output terminal of the voltage follower circuit 38 a fixed reference voltage $V_R$ representative of a predetermined value of the cell voltage $V_S$ as selected or calculated by the control circuit 30.

Subsequent to the reference voltage generator network 34 a pump signal supply network 40 is provided to produce the pump current $I_P$ to be supplied to the oxygen pump stack 12 of the oxygen sensor unit 10. The pump signal supply network 40 comprises an operational amplifier 42 having an inverting input terminal and a non-inverting input terminal which is connected through a resistor 44 to the output terminal of the reference voltage generator network 34. The operational amplifier 42 thus receives the reference voltage $V_R$ at its non-inverting input terminal and has its output terminal connected through a resistor 46 to the base of an n-p-n bipola transistor 48. The n-p-n transistor 48 has its collector connected to the conductive strip portion 16a of the inner electrode plate 16 of the oxygen pump stack 12 of the oxygen sensor unit 10 as shown and its emitter connected on one hand to the pump signal input terminal $S_P$ of the control circuit 30 and on the other hand grounded through a resistor 50. The conductive strip portion 18a of the outer electrode plate 18 of the oxygen pump stack 12 of the oxygen sensor unit 10 is connected to a predetermined bias voltage $V_B$ of the positive polarity so that the inner electrode plate 16 of the oxygen pump stack 12 is biased to the negative polarity with respect to the outer electrode plate 18 of the stack 12. When the transistor 48 is in a conduction state, the collector current of the transistor 48 is supplied as the pump current $I_P$ to the oxygen pump stack 12 of the oxygen sensor unit 10 and produces across the resistor 50 a d.c. pump voltage $V_P$ which is variable with the pump current $I_P$. This pump voltage $V_P$ is supplied to the pump signal input terminal $S_P$ of the control circuit 30 and is memorized in the RAM included in the control circuit 30 as previously noted.

On the other hand, the sensor cell stack 14 of the oxygen sensor unit 10 has the conductive strip portion 22a of its inner electrode plate 22 connected to ground and the conductive strip portion 24a of its outer electrode plate 24 connected through a noise filter 52 to a buffer amplifier network 54. The noise filter 52 is provided to eliminate the noise component in the voltage signal resulting from the electromotive force created across the active layer 26 of the sensor cell stack 14 and consists of a combination of a resistor 56 and a capacitor 58 as shown. The buffer amplifier network 54 comprises an operational amplifier 60 having its non-inverting input terminal connected through the noise filter 52 to the outer electrode plate 24 of the sensor cell stack 14 of the oxygen sensor unit 10 and its inverting input terminal connected through a feedback resistor 62 to the output terminal of the amplifier 60 and through a resistor 64 to ground. Thus, the operational amplifier 60 serves as a non-inverting, active-gain buffer amplifier producing an amplified cell voltage $V_S'$ at its output terminal. The output terminal of the operational amplifier 60 is connected not only through the feedback resistor 62 to the inverting input terminal of the amplifier 60 but also through a resistor 66 to the inverting input terminal of the operational amplifier 42 in the pump signal supply network 40. The operational amplifier 42 of the signal supply network 40 is thus operative as a comparator producing a voltage output of a high level when the reference voltage $V_R$ appearing at the non-inverting input terminal thereof is higher than the amplified cell voltage $V_S'$ appearing at the inverting input terminal thereof and a voltage output of a low level when the reference voltage $V_R$ is lower than the amplified cell voltage $V_S'$.

Where the oxygen concentration detection system thus constructed uses temperature adjust means including the insulating layers provided with heat generating elements as previously discussed, the temperature adjust means further comprises a temperature control network including a temperature sensor such as a thermocouple located in conjunction with the sensor unit 10 to detect the temperature of the sensor unit 10. Such a temperature control network may also be connected across the resistor 50 to produce a temperature compensation current on the basis of the pump voltage $V_P$ produced in the network 40 and the temperature detected by the temperature sensor.

Operation

Throughout operation of the oxygen concentration detection system constructed and arranged as hereinbefore described, the control circuit 30 is producing a digital signal representative of the value at which the cell voltage $V_S$ is to be maintained. The digital signal is fed from the reference signal output terminal $S_R$ of the control circuit 30 to the reference voltage generator network 34 and is converted by the digital-to-analog converter 36 into a fixed reference voltage $V_R$. The reference voltage $V_R$ is passed through the voltage follower 38 to the non-inverting input terminal of the operational amplifier 42 in the pump signal supply network 40 by way of the resistor 44. Assuming for purposes of description that the amplified cell voltage $V_S'$ appearing at the inverting input terminal of the operational amplifier 42 is lower than the reference voltage $V_R$ at a particular point of time, the operational amplifier 42 operating as a comparator produces an output voltage of a high level. The high output voltage of the operational amplifier 42 is applied to the base of the transistor 46, which is accordingly made conductive and provides a current path through the collector and emitter thereof.

The oxygen sensor unit 10 being located within the exhaust manifold of the engine, the exhaust gases discharged from the power cylinders into the exhaust manifold of the engine are partially admitted into the gap between the pump and cell stacks 12 and 14 of the sensor unit 10. With the collector current of the transistor 48 now flowing through the oxygen pump stack 12 of the oxygen sensor unit 10, oxygen ions are caused to migrate through the oxygen-ion conductive active layer 20 of the oxygen pump stack 12 away from the negative inner electrode plate 16 toward the positive outer electrode plate 18 of the stack 12. As a result of such movement of oxygen ions through the active layer 20 of the oxygen pump stack 12, the oxygen molecules contained in the exhaust gases in the gap between the pump and cell stacks 12 and 14 are caused to diffuse into the active layer 20 through the inner electrode plate 16, urging the oxygen molecules in the active layer 20 to move out of the layer 20 through the outer electrode plate 18 of the oxygen pump stack 12. As the oxygen molecules are thus pumped out of the gap between the pump and cell stacks 12 and 14, there is produced a gradual decrease in the concentration of oxygen in the gases staying in the gap so that a differential grows between the concentrations of oxygen in the gases in the gap and in the ambient gases in which the sensor unit 10 is immersed within the exhaust manifold of the engine. Upon lapse of a certain incipient transient period, a steady state is reached at which the number of the oxygen molecules pumped out of the gap between the stacks 12 and 14 is equalized with the number of the oxygen molecules allowed into the gap. Under such a steady state condition, the average pumped oxygen partial pressure in the gap between the stacks 12 and 14 assumes a value (assumed to be uniform throughout the gap) which is smaller than the non-pumped oxygen partial pressure in the ambient exhaust gases surrounding the oxygen sensor unit 10. The differential oxygen partial pressure thus developed between the gases inside the gap and the gases outside the gap acts on the oxygen-ion conductive active layer 26 of the sensor cell stack 14. The sensor cell stack 14 is accordingly caused to induce across the active layer 26 thereof an electromotive force which varies with the differential between the pumped and non-pumped oxygen partial pressures, thereby producing the cell voltage $V_S$ between the inner and outer electrode plates 22 and 24 of the sensor cell stack 14. It will be understood that the cell voltage $V_S$ thus produced by the sensor cell stack 14 of the oxygen sensor unit 10 is variable with the differential between the pumped and non-pumped oxygen partial pressures in the oxygen sensor unit 10.

The cell voltage $V_S$ is supplied through the noise filter 52 to the non-inverting input terminal of the operational amplifier 60 in the buffer amplifier network 54. The operational amplifier 60 produces at its output terminal the amplified cell voltage $V_S'$ continuously variable with the cell voltage $V_S$ received from the oxygen sensor unit 10. This amplified cell voltage $V_S'$ is fed to the inverting input terminal of the operational amplifier 42 in the pump signal supply network 40 and is compared with the reference voltage $V_R$ appearing at the non-inverting input terminal of the operational amplifier 42. If the cell voltage $V_S$ from the oxygen sensor unit 10 is increasing at a particular point of time and accordingly the amplified cell voltage $V_S'$ supplied to the operational amplifier 42 of the pump signal supply network 40 exceeds the reference voltage $V_R$, the operational amplifier 42 produces an output voltage of a low level and holds the transistor 48 in a non-conduction state. The transistor 48 being in the non-conduction state, there is substantially no flow of current through the collector of the transistor 48 with a consequent decrease in the cell voltage $V_S$ across the sensor cell stack 14 of the oxygen sensor unit 10 and accordingly in the amplified cell voltage $V_S'$ appearing at the inverting input terminal of the operational amplifier 42 in the signal supply network 40. When the amplified cell voltage $V_S'$ at the inverting input terminal of the operational amplifier 42 thereafter becomes lower than the reference voltage $V_R$ at the non-inverting input terminal of the amplifier 42, the transistor 48 is enabled to turn on and gives rise to an increase in the collector current. The transistor 48 repeats such switching actions at a high frequency so that the cell voltage $V_S$ developed across the sensor cell stack 14 of the oxygen sensor unit 10 is maintained at a fixed level with the collector current of the transistor 48 varied in linearly proportional relationship to the percent concentration of the oxygen in the gases surrounding the oxygen sensor unit 10, as will be seen from FIG. 1. This collector current is applied as the pump current $I_P$ to the oxygen pump stack 12 of the oxygen sensor unit 10 and flows, by way of the emitter of the transistor 48, through the resistor 50. In FIG. 1, plots a, b and c indicate examples of such linear variation of the pump current $I_P$ with the detected concentration of oxygen when the reference voltage $V_R$ is selected or calculated by the control circuit 30 such that voltages of 20, 40 and 80 millivolts are to be produced each as the cell voltages $V_S$ across the sensor cell stack 14 of the oxygen sensor unit 10. The partially hatched area with a boundary above plot d indicates the range in which the pump current $I_P$ at a given oxygen concentration would cause the blackening of the active layer 20 of the oxygen pump stack 12 of the oxygen sensor unit 10.

To achieve the pump current $I_P$ which varies correctly in proportion to the detected concentration of the oxygen, it is important that the temperature of the oxygen sensor unit 10 be maintained at a fixed value. For this purpose, the current to be supplied to the heat generating elements of the previously mentioned temperature adjust means is controlled depending upon the pump voltage $V_P$ or pump current $I_P$ and the output signal from the temperature sensor to provide accurate temperature compensation for the pump current $I_P$. The heat applied to the pump and cell stacks 12 and 14 is effective not only to provide such temperature compensation but also to promote the electrochemical activity of the oxygen-ion conductive solid electrolyte forming the active layer of each stack, particularly the oxygen pumping activity of the oxygen pump stack 12 especially at low temperatures of the exhaust gases to which the oxygen sensor unit 10 is to be exposed. Where the temperature compensation for the pump current is not a serious requirement, the temperature adjust means might therefore be dispensed with although this would be detrimental to the electrochemical activities of the pump and cell stacks 12 and 14.

Figure 3:
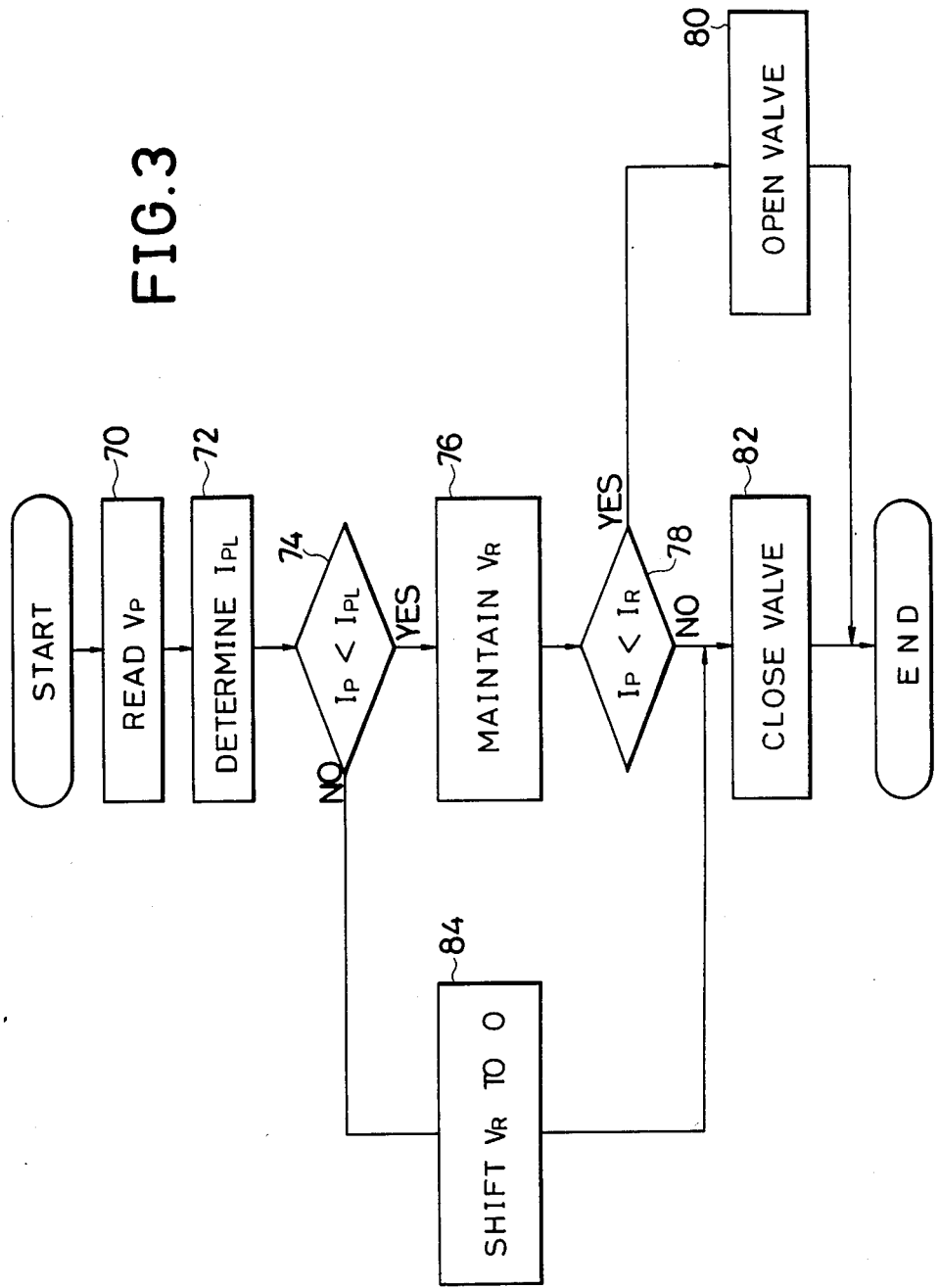
FIG. 3 is a flowchart showing a cycle of operation to be performed by the microprocessor constituting the control circuit in the circuit arrangement of the first preferred embodiment of the present invention.

The control circuit 30 implemented by a microprocessor is clocked in relation to the speed of revolution of the engine and repeats the cycle of operation illustrated in the form of a flowchart in FIG. 3. Referring to FIG. 3, the cycle of operation of the control circuit 30 starts with a process step 70 to read the pump voltage $V_P$ memorized in the RAM forming part of the control circuit 30. The control circuit 30 then proceeds to a process step 72 to calculate a function representative of an upper limit value $I_{PL}$ of the pump current $I_P$ corresponding to the voltage $V_P$. The function thus representing the upper limit value $I_{PL}$ of the pump current $I_P$ is determined (e.g. calculated, selected or assigned in the control circuit 30) to be slightly less than the critical value of the pump current $I_P$ represented by the boundary indicated by plot d in FIG. 1 and to be the smaller as the detected concentration of oxygen becomes smaller. The process step 72 is followed by a decision step 74 to determine whether or not the pump current $I_P$ corresponding to the pump voltage $V_P$ currently memorized by the RAM in the control circuit 30 is less than the limit value $I_{PL}$ of the pump current $I_P$ calculated in the preceding step 72.

If the pump current $I_P$ is found to be less than the limit value $I_{PL}$, then it is determined in a subsequent process step 76 to maintain the digital signal at the output terminal $S_R$ of the control circuit 30 and accordingly the reference voltage $V_R$ from which the particular pump current $I_P$ has resulted. In this instance, it is further determined in a decision step 78 whether or not the pump current $I_P$ in question is less than a current value $I_R$ indicative of a target air-to-fuel ratio of the mixture to be supplied to the engine at the present point of time. This current value $I_R$ is calculated from the reference voltage $V_R$ resulting from the digital signal appearing at the output terminal $S_R$ of the control circuit 30. If the pump current $I_P$ is found to be less than the current value $I_R$ thus calculated, it is determined in a process step 80 that the mixture which is currently being fed to the engine is excessively rich and that the secondary-air introducing valve 32 (FIG. 2) should be open. The secondary-air introducing valve 32 is thus actuated to open if the valve has been closed or is allowed to remain open if the valve has been in the open condition. If, on the contrary, the pump current $I_P$ is found to be not less than the current value $I_R$ in the decision step 78, it is determined in a subsequent process step 82 that the mixture being fed to the engine is excessively lean and that the secondary-air introducing valve 32 should be closed. The secondary-air introducing valve 32 is accordingly operated to close if the valve has been open or is allowed to remain closed if the valve has been in the closed condition.

If, on the other hand, the pump current $I_P$ corresponding to the pump voltage $V_P$ read from the RAM is found to be not less than the limit value $I_{PL}$ in the decision step 74, then it is determined in a process step 84 to alter the digital signal at the output terminal $S_R$ of the control circuit 30 to a new one effective to produce zero volts as the reference voltage $V_R$. In the circuitry shown in FIG. 2, the zero volt reference voltage $V_R$ thus produced by the reference signal generator 34 is passed through the resistor 44 to the non-inverting input terminal of the operational amplifier 42 in the pump signal supply network 40. The operational amplifier 42 then produces an output voltage of a low level and causes the transistor 48 to turn off, thereby interrupting the supply of collector current to the oxygen pump stack 12 of the oxygen sensor unit 10. In this instance, the process step 84 proceeds to the process step 82 to cease the supply of current to the secondary-air introducing valve 32 and cause the valve to close.

A single cycle of operation of the microprocessor constituting the control circuit 30 thus terminates with the process step 80 or 82 to shift the air-to-fuel ratio of the mixture either to the lean burn side or to the rich burn side depending upon the pump current $I_P$ produced in the pump signal supply network 40. The new digital signal to be produced in the process step 84 to shift the reference voltage $V_R$ to zero volts as described above may be in the form of a four-bit signal of, for example, "0000". Alternatively, the means to produce such a new digital signal to alter the reference voltage $V_R$ may be substituted by means operative to have the non-inverting input terminal of the operational amplifier 42 forcibly grounded or to otherwise build up a zero volt potential at the non-inverting input terminal of the operational amplifier 42.

SECOND PREFERRED EMBODIMENT

Construction and Arrangement

Figure 4:
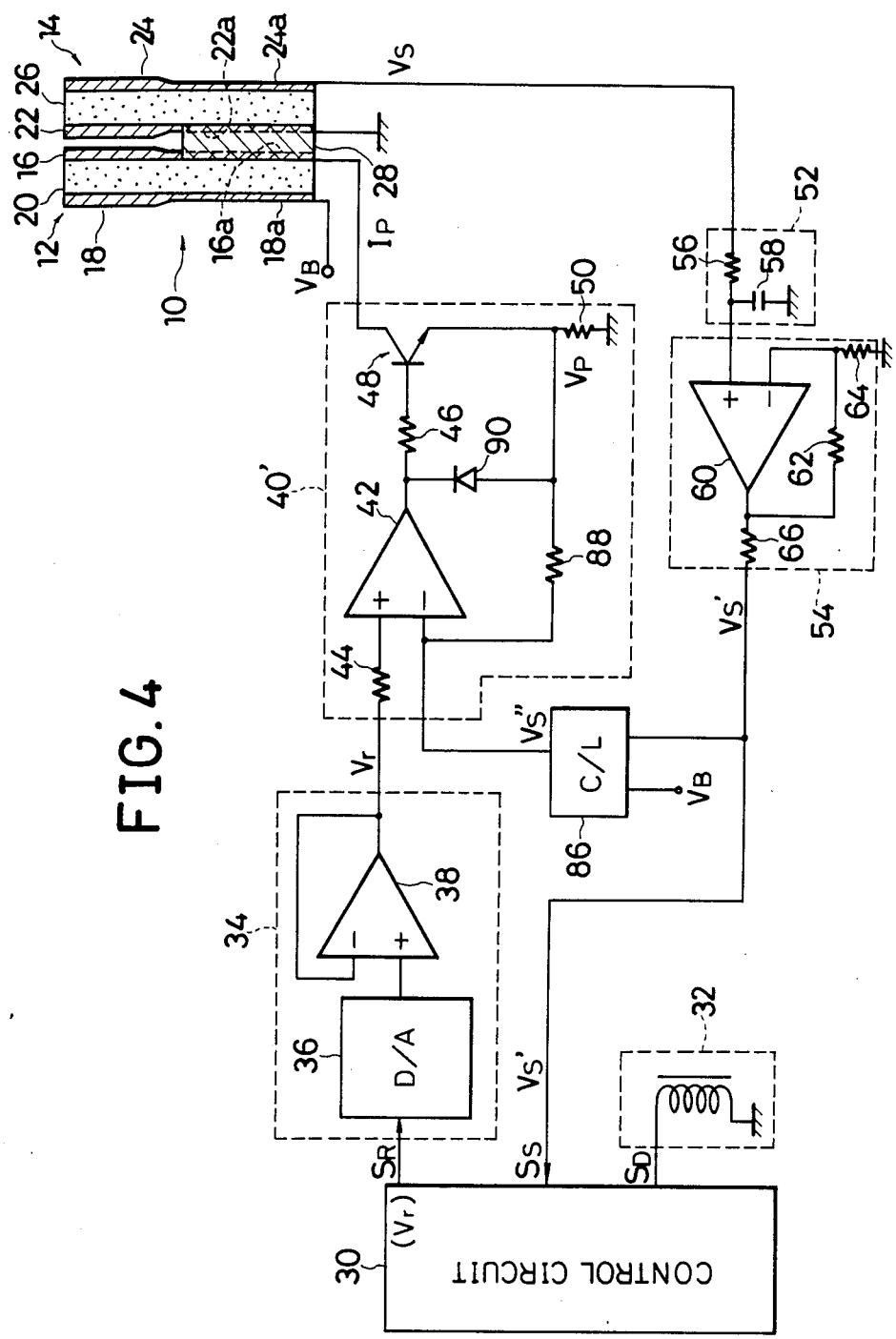
FIG. 4 is a view similar to FIG. 2 but shows the general circuit arrangement of a second preferred embodiment of a oxygen concentration detection system according to the present invention with the oxygen sensor unit of the system also shown in section.

FIG. 4 of the drawings shows a second preferred embodiment of an oxygen concentration detection system according to the present invention. The embodiment herein shown is similar to the first preferred embodiment except for the construction and arrangement of the pump signal generator network and further for the addition of a pump current limiter network 86. Furthermore, the control circuit 30 provided in the embodiment shown in FIG. 4 has, in addition to the reference signal output terminal $S_R$ and the valve drive terminal $S_D$, a cell signal input terminal $S_S$ in lieu of the pump signal input terminal $S_P$ of the control circuit 30 in the embodiment of FIG. 2. The digital signal supplied from the reference signal output terminal $S_R$ represents a value selected or calculated by the control circuit 30 and is used to produce a first reference voltage $V_r$ in the second embodiment of the present invention. At the cell signal input terminal $S_S$ is to appear a voltage variable with the cell voltage $V_S$ produced by the sensor cell stack 14 of the oxygen sensor unit 10 will be seen as the description proceeds. The voltage supplied to this input terminal $S_S$ is memorized in the RAM (not shown) incorporated in the microprocessor constituting the control circuit 30 and is to be compared with a second reference voltage $V_r'$ which represents a target air-to-fuel ratio to which the mixture to be supplied to the engine is to be proportioned. The digital signal to be supplied from the reference signal output terminal $S_R$ is selected or calculated by the control circuit 30.

Unlike the pump signal supply network 40 in the embodiment of FIG. 2, the pump signal supply network, now denoted by 40' in the embodiment shown in FIG. 4, is adapted to produce a pump current $I_P$ of a fixed level in response to the first reference voltage $V_r$ so that the cell voltage $V_S$ is variable with the concentration of the oxygen in the ambient exhaust gases. For this purpose, the operational amplifier 42 of the pump signal supply network 40' has its inverting input terminal connected to the emitter of the transistor 48 through a feedback resistor 88. Thus, a voltage proportional to the pump voltage $V_P$ which appears across the resistor 50 is applied to the inverting input terminal of the operational amplifier 42 in lieu of the amplified cell voltage $V_S'$ supplied from the buffer amplifier network 54 in the embodiment of FIG. 2. A diode 90 is provided which has its anode connected to the emitter of the transistor 48 and its cathode connected to the output terminal of the operational amplifier 42. Furthermore, the operational amplifier 60 of the the buffer amplifier network 54 has its output terminal connected via the resistor 66 to the cell signal input terminal $S_S$ of the control circuit 30. On the other hand, the pump current limiter network 86 additionally provided in the embodiment herein shown has one input terminal connected to the output terminal of the operational amplifier 60 in the buffer amplifier network 54 through the resistor 66 and another input terminal connected to a source of a fixed positive d.c. voltage $V_B$. The pump current limiter network 86 further has an output terminal connected to the inverting input terminal of the operational amplifier 42 in the pump signal supply network 40' and accordingly through the resistor 88 to the anode of the diode 90 as shown. The pump current limiter network 86 thus arranged between the signal supply network 40' and the buffer amplifier network 54 is operative to reduce the amplified cell voltage $V_S'$ from the buffer amplifier network 54 by a selected value and is preferably constructed as shown in FIG. 5.

Figure 5:
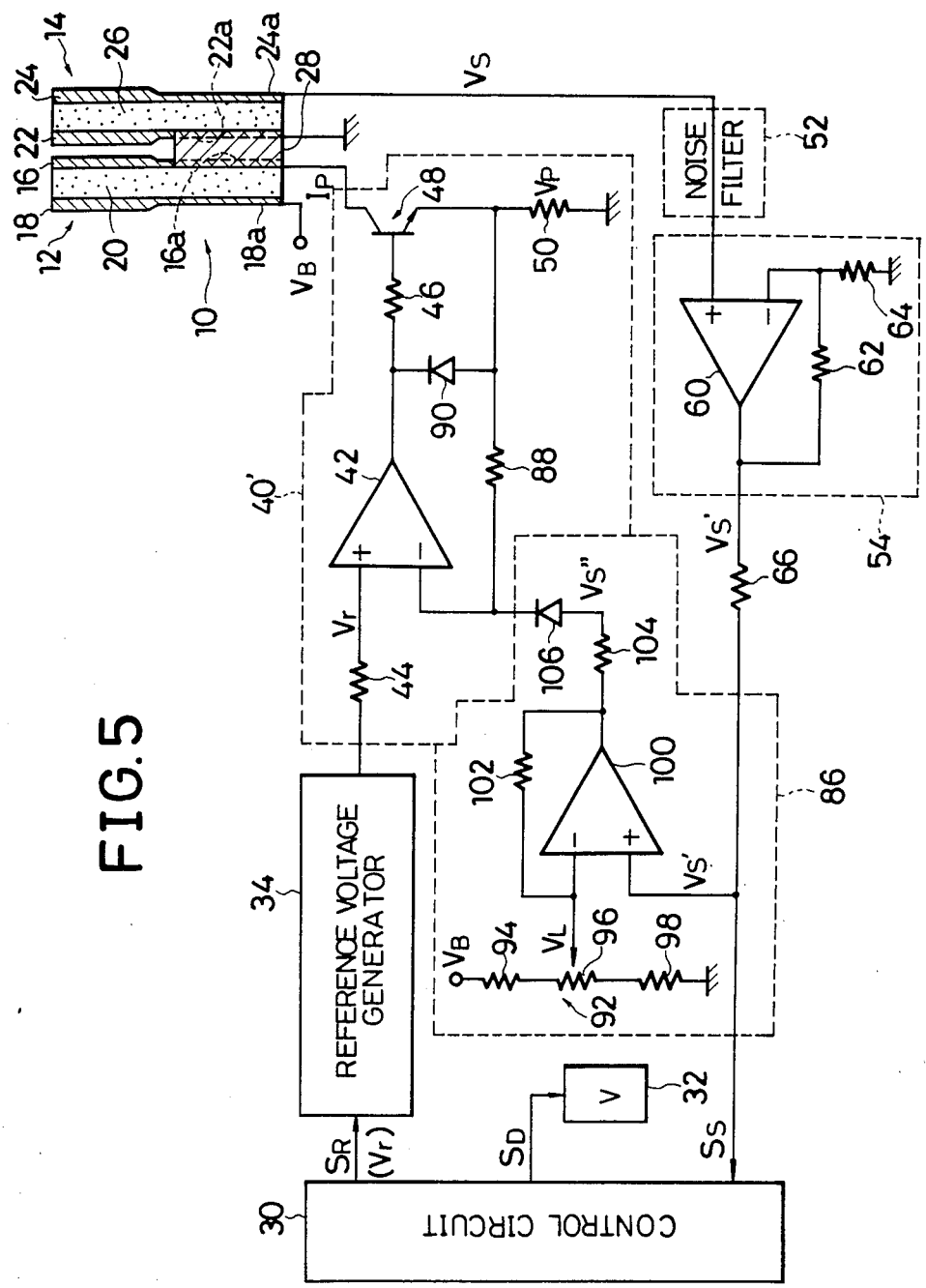
FIG. 5 is a block diagram showing in more detail the oxygen concentration detection system illustrated in FIG. 4.

Turning to FIG. 5, the pump current limiter network 86 comprises an adjustable voltage divider circuit 92 shown consisting of a series combination of resistors 94, 96 and 98 connected between ground and the above mentioned source of the fixed d.c. voltage $V_B$. The resistor 96 is connected between the remaining two resistors 94 and 98 and constitutes a variable resistor producing a fractional voltage $V_L$. The fractional voltage $V_L$ to be produced by means of the adjustable divider circuit 92 is selected to be slightly higher than the second reference voltage $V_r'$ set in the control circuit 30. The pump current limiter network 86 further comprises a differential operational amplifier 100 having its non-inverting input terminal connected through the resistor 66 to the output terminal of the operational amplifier 60 in the buffer amplifier network 54 and its inverting input terminal connected to the variable resistor 96 and through a feedback resistor 102 to the output terminal of the amplifier 100. Thus, the differential operational amplifier 100 is operative as a subtractor producing a reduced cell voltage $V_S''$ which is lower by the variable fractional voltage $V_L$ than the amplified cell voltage $V_S'$ supplied from the operational amplifier 60 of the buffer amplifier network 54. The output terminal of the operational amplifier 100 is connected not only through the feedback resistor 102 to the inverting input terminal of the amplifier 100 but also through a resistor 104 and a diode 106 to the inverting input terminal of the operational amplifier 42 in the pump signal supply network 40' and further through the resistor 88 to the anode of the diode 90 as shown.

Operation

The reference voltage $V_r$ is produced by the reference voltage generator network 34 from the digital signal supplied from the reference signal output terminal $S_R$ of the control circuit 30 as in the embodiment described with reference to FIG. 2. The reference voltage $V_r$ is passed to the non-inverting input terminal of the operational amplifier 42 in the pump signal supply network 40' by way of the resistor 44. If the pump voltage $V_P$ appearing across the resistor 50 and accordingly at the inverting input terminal of the operational amplifier 42 becomes lower than the reference voltage $V_r$ at a particular point of time, the operational amplifier 42 produces an output voltage of a high level and causes the transistor 48 to turn on. If, on the other hand, the pump voltage $V_P$ becomes higher than the reference voltage $V_r$, then the operational amplifier 42 produces an output voltage of a low level and causes the transistor 48 to turn off. By repetition of such turn-on and turn-off actions at a high frequency, the pump voltage $V_P$ appearing across the resistor 50 is maintained at a constant value which is dictated by the first reference voltage $V_r$. In response to the constant pump current $I_P$ thus supplied from the pump signal supply network 40', the oxygen sensor unit 10 produces a cell voltage $V_S$ which is variable with the concentration of the oxygen contained in the ambient exhaust gases in which the sensor unit 10 is positioned.

The cell voltage $V_S$ thus produced by the sensor cell stack 14 of the oxygen sensor unit 10 is supplied through the noise filter 52 to the non-inverting input terminal of the operational amplifier 60 in the buffer amplifier network 54. The operational amplifier 60 thus produces at its output terminal the amplified cell voltage $V_S'$, which is fed through the resistor 66 to the cell signal input terminal $S_S$ of the control circuit 30 and to the non-inverting input terminal of the operational amplifier 100 in the pump current limiter network 86. The amplified cell voltage $V_S'$ supplied to the cell signal input terminal $S_S$ of the control circuit 30 is memorized in the RAM included therein and is compared with the second reference voltage $V_r'$ which represents the concentration of oxygen in the combustible mixture with a target air-to-fuel ratio to which the mixture is to be proportioned. If it is found that the amplified cell voltage $V_S'$ is found lower than the second reference voltage $V_r'$, then the control circuit 30 determines that the air-to-fuel ratio of the mixture being supplied to the engine is on the lean burn side and that the secondary-air introducing valve 32 should be closed. The secondary-air introducing valve 32 is thus operated to close if the valve 32 has been held open or is allowed to remain closed if the valve 32 has been in the closed condition. If, on the contrary, the amplified cell voltage $V_S'$ is found higher than the second reference voltage $V_r'$, the control circuit 30 determines that the air-to-fuel ratio of the mixture being fed to the engine is on the rich burn side and that the secondary-air introducing valve 32 should be open. The secondary-air introducing valve 32 is thus caused to open if the valve 32 has been closed or is allowed to remain open if the valve 32 has been in the open condition.

Assume now that the mixture to be supplied to the power cylinders of the engine happened to be suddenly enriched with the throttle valve of the induction system of the engine closed to limit the flow of air through the induction system. The sudden enrichment of the mixture is followed by a corresponding increase in the cell voltage $V_S$ generated by the sensor cell stack 14 of the oxygen sensor unit 10 and accordingly in the amplified cell voltage $V_S'$ which appears at the output terminal of the operational amplifier 60 in the buffer amplifier network 54. The amplified cell voltage $V_S'$ thus increased is fed to the non-inverting input terminal of the operational amplifier 100 in the pump current limiter network 86 and, when the voltage $V_S'$ exceeds the fractional voltage $V_L$ appearing at the inverting input terminal of the operational amplifier 100, there appears at the output terminal of the amplifier 100 a positive voltage proportional to the differential between the voltages $V_S'$ and $V_L$. The differential voltage $V_S' - V_L$ is higher than the pump voltage $V_P$ currently appearing across the resistor 50 so that a current flows from the output terminal of the operational amplifier 100 to ground by way of the resistor 104, diode 106, and resistors 88 and 50. This current gives rise to an increase in the voltage at the inverting input terminal of the operational amplifier 42 in the signal supply network 40' with a consequent decrease in the output voltage from the operational amplifier 42. The reduced voltage at the output terminal of the operational amplifier 42 makes the transistor 48 less conductive or non-conductive and causes the pump current $I_P$ to diminish or close. The leaner the mixture produced in the engine and accordingly the higher the cell voltage $V_S$ produced by the oxygen sensor unit 10, the higher will the output voltage from the operational amplifier 100 become. The voltage $V_L$ produced by the adjustable voltage divider circuit 92 being selected to be slightly higher than the second reference voltage $V_r'$ set in the control circuit 30 as previously noted, the amplified cell voltage $V_S'$ higher than the fractional voltage $V_L$ is predictive of a condition in which the pump current $I_P$ is approaching a value which may cause the blacking of the active layer 20 of the oxygen pump stack 12 of the oxygen sensor unit 10. The reduction in the pump current $I_P$ in response to an abrupt increase in the cell voltage $V_S$ as effected as discussed above is thus effectively contributory to prevention of the blackening of the active layer 20 of the oxygen pump stack 12.

When the amplified cell voltage $V_S'$ is lower than the variable fractional voltage $V_L$, there appears at the output terminal of the amplifier 100 a negative voltage proportional to the differential between the voltages $V_S'$ and $V_L$. The negative output voltage of the operational amplifier 100 is precluded from flowing beyond the diode 106 so that the operational amplifier 42 of the signal supply network 40' acts solely in response to the first reference voltage $V_r$ and the pump voltage $V_P$ which appears across the resistor 50. Thus, the transistor 48 is turned on when the pump voltage $V_P$ is lower than the first reference voltage $V_r$ and turned off when the pump voltage $V_P$ is higher than the first reference voltage $V_r$.

Figure 6:
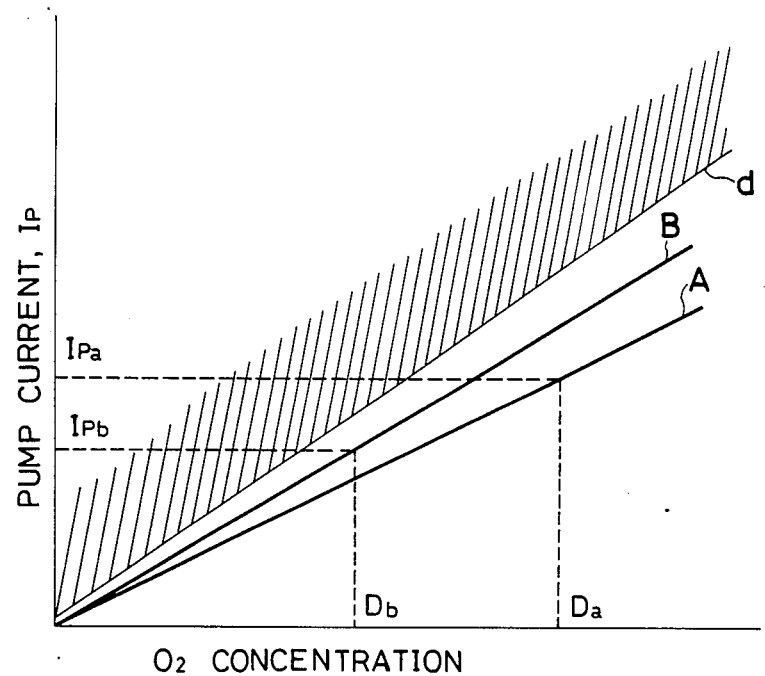
FIG. 6 is a graphic representation of examples of the relationship between the concentration of oxygen to which the oxygen sensor unit is subjected and the pump current ($I_P$) produced in response to the oxygen concentration during operation of the system shown in FIGS. 4 and 5, and further shows the critical value of the pump current ($I_P$) as shown in FIG. 1.

The pump current $I_P$ to be produced with the second reference voltage $V_r'$ set at a given value may be controlled to vary with the concentration of oxygen in the ambient exhaust gases as represented by plot "A" in FIG. 6 in the embodiment hereinbefore described. In this instance, the pump current $I_P$ to be supplied to the oxygen sensor unit 10 assumes a value $I_{Pa}$ when the concentration of oxygen assumes a value $D_a$ which corresponds to the target air-to-fuel ratio represented by the reference voltage $V_r'$. The pump current $I_P$ thus controlled may have an upper limit value which varies with the concentration of oxygen in the ambient exhaust gases as represented by plot "B" in FIG. 6 when the fractional voltage $V_L$ produced in the pump current limiter network 86. In the event the mixture to be supplied to the engine is suddenly enriched so that the air-to-fuel ratio of the mixture is reduced significantly, the concentration of the oxygen represented by the cell voltage $V_S$ may be of the order of a value indicated at $D_b$ on plot "B" in FIG. 6. If the pump current $I_P$ were maintained unchanged at the value $I_{Pa}$ under these conditions, the pump current $I_P$ would have a value which might cause blackening of the oxygen-ion conductive solid electrolyte used as the active material in the oxygen sensor unit 10. The pump current $I_P$ being limited below the level of the plot "B" by virtue of the pump current limiter network 86, the pump current can not exceed the value indicated at $I_{Pb}$ on the plot "B" and for this reason the occurrence of the blackening can be precluded in the oxygen sensor unit 10.

What is claimed is:

1. An oxygen concentration detection system comprising:
    a sensor including a pump cell element and a sensor cell element, each said element having a pair of electrodes disposed on opposing sides of a solid electrolyte layer, said pump cell element and said sensor cell element being positioned adjacent a restricted region, said pump cell element transferring oxygen into said restricted region in accordance with a pump current supplied thereto, said sensor cell element producing a sensor voltage representing an oxygen concentration within said restricted regon;
    pump current supply means, operatively connected to said sensor, for supplying a pump current to said pump cell element, said pump current supply being responsive to said sensor voltage to regulate said pump current to maintain said sensor voltage substantially at a reference level;
    oxygen concentration detecting means for detecting said oxygen concentration from said pump current; and
    excess current preventive menans, responsive to said pump current, for comparing said pump current with a predetermined discrimination value which varies in accordance with the detected oxygen concentration and for reducing said pump current when said pump current exceeds said predetermined discrimination value.

2. The oxygen concentration detection system of claim 1 wherein said excess current preventive means functions as electrolyte layer blackening prevention means by preventing pump current from exceeding a level sufficient to blacken and thereby damage said electrolyte layer due to excessive oxygen concentration.

3. An oxygen concentration detection system according to claim 1, in which said predetermined discrimination value decreases as the said detected oxygen concentration decreases.

4. An oxygen concentration detection system according to claim 1, in which said excess current preventive means reduces said pump current by asdjusting said reference level when said pump current exceeds said predetermined discrimination value.

5. An oxygen concentration detections system comprising:
  a sensor including a pump cell element and a sensor cell element, each said element having a pair of electrodes disposed on opposing sides of a solid electrolyte layer, said pump cell element and said sensor cell element being positioned adjacent a restricted region, said pump cell element transferring oxygen into said restricted region in accordance with a pump current supplied thereto, said sensor cell element producing a sensor votlage representing an oxygen concentration within said restricted region across the electrodes thereof;
  pump current supply means, operatively connected to said sensor, for supplying a pump current to said pump cell element, said pump current supply means being responsive to said sensor voltage to regulate said pump current to maintain said pump current substantially at a reference level;
  oxygen concentration detecting means for detecting said oxygen concentration from said sensor voltage; and
  excess current preventive means, responsive to said pump current, for comparing said sensor voltage with a predetermined discrimination value which varies in accordance with the detected oxygen concentration and for reducing said pump current when said sensor voltage exceeds said predetermined discrimination value.

6. The oxygen concentration detection system of claim 5 wherein said excess current preventive means functions as electrolyte layer blackening prevention means by preventing pump current from exceeding a level sufficient to blacken and thereby damage said electrolyte layer due to excessive oxygen concentration.

7. An oxygen concentration detection system according to claim 5, wherein said pump current supply means compares a pump voltage representative of said pump current with a reference voltage corresponding to said reference level;
  said excess current preventive means reducing said pump current by adjusting said pump voltage in accordance with said sensor voltage as long as said sensor voltage exceeds said predetermined discrimination value.

8. An oxygen concentration detection system according to claim 5, wherein said oxygen concentration means compares said sensor voltage with a reference voltage for detecting the oxygen concentration, said reference voltage being slightly smaller than said predetermined discrimination value.

* * * * *